(12) United States Patent
Urich

(10) Patent No.: US 6,706,020 B1
(45) Date of Patent: Mar. 16, 2004

(54) SYRINGES AND INJECTORS INCORPORATING MAGNETIC FLUID AGITATION DEVICES

(75) Inventor: Klaus Urich, Berlin (DE)

(73) Assignee: Schering Aktiengesellschaft, Berlin (DE)

(*) Notice: Subject to any disclaimer, the term of this patent is extended or adjusted under 35 U.S.C. 154(b) by 0 days.

(21) Appl. No.: 09/763,647

(22) PCT Filed: Aug. 26, 1999

(86) PCT No.: PCT/EP99/06289
§ 371 (c)(1),
(2), (4) Date: Apr. 19, 2001

(87) PCT Pub. No.: WO00/12157
PCT Pub. Date: Mar. 9, 2000

(30) Foreign Application Priority Data

Aug. 28, 1998 (DE) .......................................... 198 40 536

(51) Int. Cl.[7] ............................................. A61M 5/315
(52) U.S. Cl. ...................................................... 604/218
(58) Field of Search ...................... ; 128/218; 424/9.52; 600/431; 604/218; A61B 8/00; B01F 5/06; A61M 5/315

(56) References Cited

U.S. PATENT DOCUMENTS

| | | | |
|---|---|---|---|
| 3,604,417 A | | 9/1971 | Stolzenberg |
| 3,789,670 A | * | 2/1974 | Rosenwald ............... 73/422 |
| 3,831,903 A | | 8/1974 | Harmel, Jr. |
| 3,880,138 A | | 4/1975 | Wootten et al. |
| 4,008,718 A | | 2/1977 | Pitesky |
| 4,172,457 A | | 10/1979 | Choksi et al. |
| 4,687,000 A | | 8/1987 | Eisenhardt et al. |
| 4,784,297 A | | 11/1988 | Katz |
| 4,846,786 A | | 7/1989 | Freed et al. |
| 5,240,322 A | | 8/1993 | Haber et al. |

(List continued on next page.)

FOREIGN PATENT DOCUMENTS

| | | | |
|---|---|---|---|
| DE | 34 11 427 | 10/1985 | |
| DE | 3934024 A1 | * 12/1989 | ............ G01N/1/10 |
| DE | 39 34 024 | 4/1991 | |
| DE | 29622313 | * 12/1996 | .......... A61M/5/142 |
| DE | 296 22 313 | 3/1997 | |
| DE | 196 25 102 | 8/1997 | |
| EP | 0 033 292 | 7/1984 | |
| EP | 0 770 352 | 5/1997 | |
| WO | WO 96/18420 | 6/1996 | |
| WO | WO 97/18845 | 5/1997 | |
| WO | WO 98/22168 | 5/1998 | |
| WO | WO 98/33538 | 8/1998 | |
| WO | WO 99/27981 | 6/1999 | |
| WO | WO 00/12157 | 3/2000 | |
| WO | WO 00/12158 | 3/2000 | |
| WO | WO 00/53242 | 9/2000 | |

OTHER PUBLICATIONS

"Selective Destruction of Contrast Agent Microspheres," Bouakaz, et al., IEEE Ultrasonics Symposium, pp. 1693–1696, (1999).

(List continued on next page.)

Primary Examiner—Henry Bennett
Assistant Examiner—Sabrina Dagostino
(74) Attorney, Agent, or Firm—Gregory L. Bradley (57) ABSTRACT

A syringe for use with an injector includes a body comprising a distal discharge end, a plunger movably disposed within the body, and an agitation element disposed within the body between the plunger and the distal discharge end. The agitation element is acted on by a magnetic field to agitate the contents of the syringe. The magnetic field is generated by a source operably associated with the syringe or the injector. Preferably, the syringe contains an ultrasound contrast agent that is agitated by the agitation element. An injector system and a method for agitating the contents of a syringe are also provided.

74 Claims, 5 Drawing Sheets

U.S. PATENT DOCUMENTS

| | | |
|---|---|---|
| 5,352,036 A | 10/1994 | Haber et al. |
| 5,360,410 A | 11/1994 | Wacks |
| 5,383,858 A | 1/1995 | Reilly et al. |
| 5,401,253 A | 3/1995 | Reynolds |
| 5,425,580 A | 6/1995 | Beller |
| 5,469,849 A | 11/1995 | Sasaki et al. |
| 5,528,923 A | 6/1996 | Ledez et al. |
| 5,601,086 A | 2/1997 | Pretlow, III et al. |
| 5,611,344 A | 3/1997 | Bernstein et al. |
| 5,686,060 A | 11/1997 | Schneider et al. |
| 5,806,519 A | 9/1998 | Evans, III et al. |
| 5,840,026 A | 11/1998 | Uber, III et al. |
| 5,846,517 A | 12/1998 | Unger |
| 6,317,623 B1 | 11/2001 | Griffiths et al. |

OTHER PUBLICATIONS

"Effect of Ultrasound on the Release of Micro–Encapsulated Drugs," Frinking, et al., Ultrasonics 36, pp. 709–712, (1998).

"A Particulate Contrast Agent With Potential for Ultrasound Imaging of Liver," Parker, et al., Ultrasound in Med. & Biol., vol. 13, No. 9, pp. 555–566 (1987).

International Search Report for Counterpart PCT Application No. PCT/EP99/06289.

* cited by examiner

SYRINGES AND INJECTORS INCORPORATING MAGNETIC FLUID AGITATION DEVICES

BACKGROUND OF THE INVENTION

The present invention relates generally to movement devices for agitating the contents of syringes and, more particularly, to syringes and injectors incorporating movement devices for agitating contrast agents disposed within the syringes.

Syringes which are prefilled with ultrasound contrast agents are clamped into injectors for injection. The syringes remain therein for several minutes to one or more hours. The duration of one or more injections, including the intervening periods between the injections, may last for more than 10 minutes Depending on the nature and composition of the contrast agent, dissociation commences at different times. During this period, the ultrasound contrast agent becomes dissociated and the phases are separated from one another. The ultrasound contrast agent as a whole is no longer homogeneous. In order to restore this homogeneity, the entire injector, including the syringe clamped therein, is moved manually. Movements of this nature are not reproducible, and sufficient homogenization is not ensured.

Ultrasound contrast agents are sensitive to transverse forces. Under excessively high forces, the particles are torn apart and destroyed. This impairs the quality of the ultrasound contrast agent. Thus, to maintain the suspension of particles in ultrasound contrast agents it is necessary to agitate the agents, but at the same time the particles must not be destroyed by the agitation.

Ultrasound contrast agents are generally described in Supplement to Diagnostic Imaging, May 1995, Advanced Ultrasound, Editor: Peter L. OGLE, Editorial Offices: 600 Harrison St. San Francisco, Calif. 94107 USA.

Glass syringes and plastic syringes are described extensively in the publication by Junga (M. JUNGA (1973) Pharm. Ind. Vol. 35, No. IIa, pages 824 to 829). A mixture of glass and plastic is described in PCT Publication No. WO 96/00098.

Injectors are generally described in EP Publication No. 0 584 531.

SUMMARY OF THE INVENTION

The present invention provides apparatuses and methods for maintaining the homogeneity and integrity of an ultrasound contrast agent over a relatively long period of time without destroying the consistency of the ultrasound contrast agent and hence impairing its pharmacological and diagnostic properties. The dissociation begins immediately after the initial preparation of the ultrasound contrast agent, and at the latest after the syringe has been inserted into the injector when the latter is at rest (i.e., is not moving). By maintaining the homogeneity and integrity of the particles suspended in the contrast agent at optimal levels, the diagnostic properties of the contrast agent can be optimized.

The present invention further provides apparatuses and methods for continuous, controlled and/or reproducible agitation procedures for contrast agents. These procedures can be utilized between the time of preparation of the contrast agents and their injection into a patient.

Further, the present invention provides agitation procedures that can be specifically designed and/or adjusted for specific contrast agents, including ultrasound contrast agents.

Also, the agitation procedures may be designed to minimize turbulent agitation of the contrast agents, thereby reducing shear forces and other stresses that could be harmful to the integrity of the particles suspended in the contrast agents.

Moreover, the present invention provides a controlled application of magnetic energy to maintain the homogeneity of the contrast agent suspension, without mixing or otherwise destroying the particles of the contrast agents.

One aspect of the present invention is achieved by means of a syringe which is filled with ultrasound contrast agent for administering the contents thereof by means of an injector, wherein at least one ferromagnetic or magnetic agitation element is arranged in the syringe. The agitation element can be exposed to a magnetic field, the source of which is arranged in the syringe, on the syringe, around the syringe in the injector or associated with an accessory for the injector, and which is movable with respect to the syringe.

Another aspect of the present invention is achieved by means of an injector or an accessory associated with an Injector, which induces or is able to induce a magnetic field that acts on at least one ferromagnetic or magnetic agitation element in the syringe. The source of the magnetic field may be arranged in the syringe, on the syringe, around the syringe, in the injector or the accessory associated therewith. Further, the direction of the lines of flux in the magnetic field may be variable with respect to the syringe.

In one embodiment, the injector accommodates the syringes which are filled with an ultrasound contrast agent via at least one holder.

In a preferred embodiment, the present invention provides a combination of a syringe filled with a contrast agent and an injector or an accessory for use with an injector. At least one ferromagnetic or magnetic agitation element is contained in the syringe and is exposed to a magnetic field, the source of which is arranged in the syringe, on the syringe, around the syringe or in the injector or an accessory associated therewith. Further, the direction of the lines of flux of the magnetic field may be three-dimensionally variable with respect to the syringe.

In another embodiment, the injector may be connected to the syringe or the injector accessory may be connected to the syringe via the injector.

In another preferred embodiment, the syringes are made from plastic, glass or a plastic/glass material. Further, the syringes may be disposable syringes.

Moreover, the agitation element may be exposed to the magnetic field via a magnetic field coupling.

The present invention, along with further aspects and attendant advantages, will best be understood by reference to the following detailed description taken in conjunction with the accompanying drawings.

DETAILED DESCRIPTION OF THE PRESENTLY PREFERRED EMBODIMENTS

Figure 1:
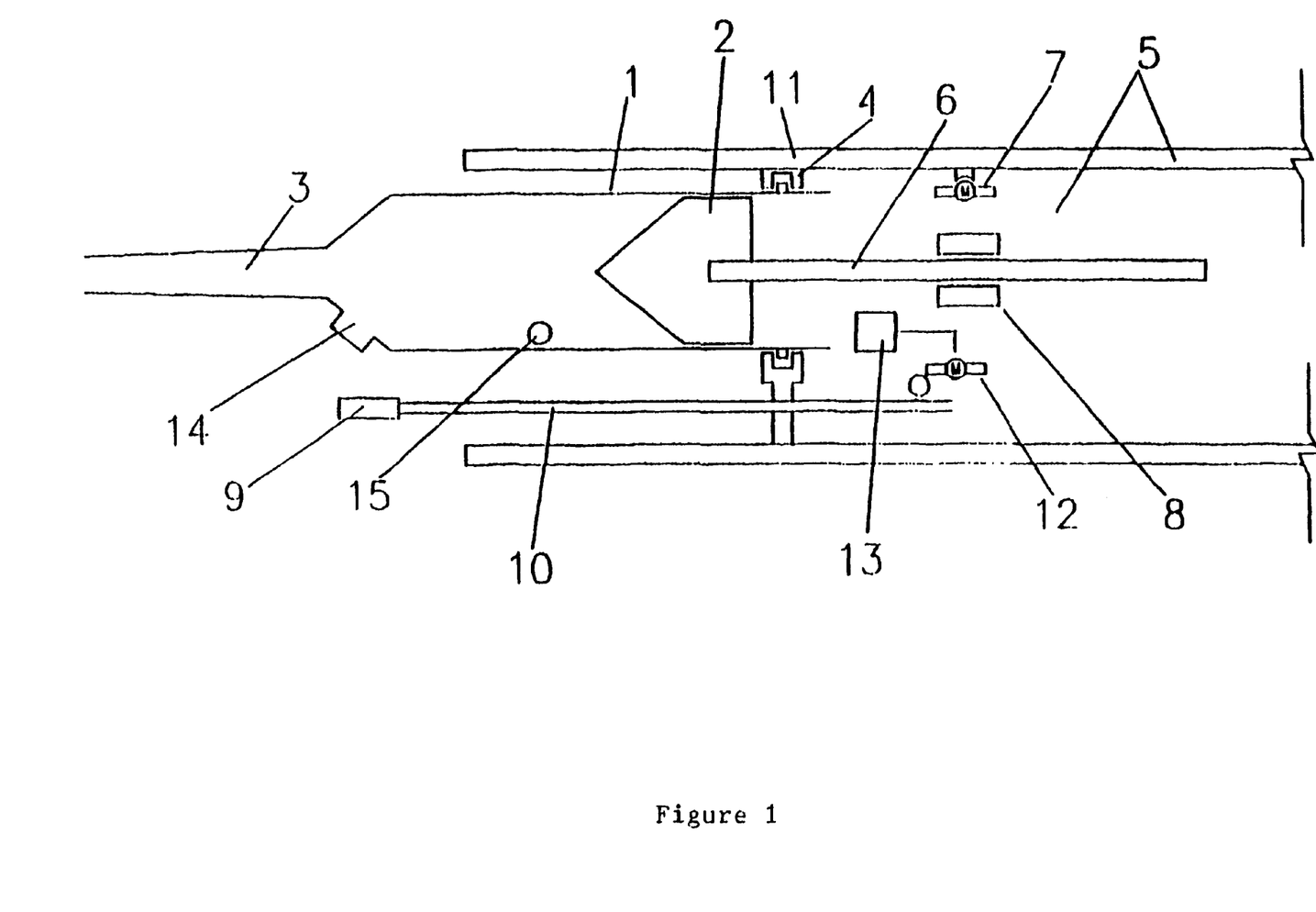
FIG. 1 is an elevated, cross-sectional view of an injector system incorporating a movable magnet.
Figure 2:
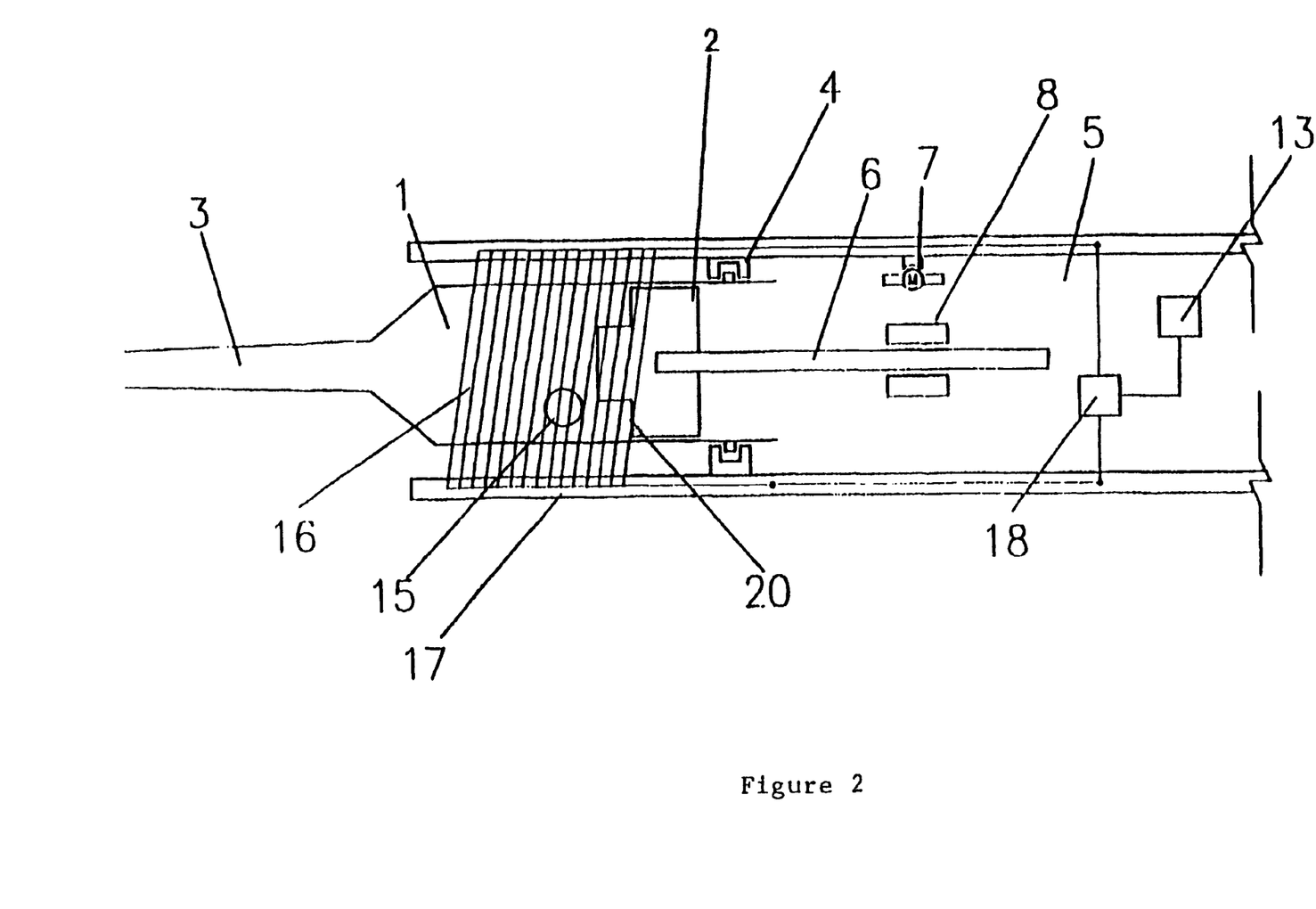
FIG. 2 is an elevated, cross-sectional view of an injector system incorporating helically running magnetic conductors.

Before turning to a detailed description of the preferred embodiments, as illustrated in FIGS. 1 and 2, the present invention is described first below in general terms applicable to all suitable embodiments thereof.

As an initial matter, the terms "syringe" and/or "syringes" as used herein can mean and encompass the following terms and devices: cartridges (large-volume syringe with a volume of at least 100 ml); ampoule syringes; disposable syringes; disposable syringe ampoules; throw-away syringe ampoules; throw-away syringes; injection ampoules; disposable injection ampoules; ready-for-injection ampoules; cylindrical ampoules; twin-chamber injection ampoules, two-chamber syringes; two-chamber syringe ampoules; and no-delay syringes.

In addition, the terms "injector" and/or "injectors" as used herein can mean and encompass the following terms and devices: infusion pumps; infusers; perfusors; and all other applicators or devices that operate to empty syringes of fluid contain therein.

Further, the terms "accessory" and/or "accessories" as used herein can mean and encompass the following: all devices which are or may be physically connected to an injector and operate to move the magnetic field in such a way that the agitation element in the syringe changes position. Typical accessories include collars, cylinders and attachments which act magnetically on the agitation element. The accessory fulfills the function of moving the agitation element by means of a magnetic force.

The magnetic field used with the present invention may preferably comprise an electromagnetic field. The electromagnetic field can be generated by means of a multiplicity of electromagnets which are arranged, for example, in the manner of a linear motor. The electromagnets may surround the syringe in the manner of a collar or sleeve. The electromagnets may also form part of the housing of the injector. The electromagnets are operable to attract an agitation element disposed within a syringe. The agitation element comprises at least one ferromagnetic or magnetic part. The arrangement of the electromagnets may be such that a linear, circular or helical movement of the agitation element, as well as mixed forms thereof, are possible.

In another embodiment, various coils can be arranged around the circumference of or within the cylinder or body of the syringe, with the current flowing through the coils at different times.

Further, the source of the magnetic field may be movably disposed outside of the syringe. In this case, the magnetic field source may comprise a magnet or a ferromagnetic element, the latter solution being possible when the agitation element is a permanent magnet.

Moreover, the magnetic field source may also be generated by means of electromagnets or coils that are situated in the wall of the syringe cylinder or body. In this embodiment, the electromagnets or coils are preferably controlled by the injector.

In the present invention, the agitation element may be encased by various substances. Suitable substances for the casing include, but are not limited to, glass and plastic materials, such as Teflon, which are preferably inert with respect to contrast agents. The use of a casing also reduces friction, which results in a reduction in or avoidance of particles within the syringe. Preferably, the agitation element is in the form of a ball.

The syringe preferably includes a recess therein for accommodating the agitation element. The recess preferably is designed in such a way that the agitation element can slide into or out of the recess. The recess preferably lies outside the movement range of the plunger in the syringe or itself forms part of the plunger.

Also, the recess may be formed both in the syringe and in the plunger. Preferably, the recess is positioned at or adjacent to the distal end (i.e., the syringe end having the needle attachment, hose attachment or luer lock fitting) of the syringe.

Further, the recess may be situated in the distal cover of the syringe cylinder or located in the syringe cylinder itself, close to the cover. In this case, a lock is preferably included to prevent the agitation element from blocking the syringe outlet.

In addition, the recess may comprise an annular recess that is disposed in the cover of the syringe cylinder. This design eliminates the need to orient the agitation element with respect to the syringe when the latter has been completely emptied.

Preferably, the recess is arranged in the syringe plunger. In this case, careful attention should be paid to the accurate orientation of the plunger with respect to the magnetic field source, unless an annular recess is situated in that part of the plunger which faces toward the needle attachment end (i.e., distal end) of the syringe.

An important feature of the syringe is the design of the plunger, the closure, and the corresponding distal opening. The syringes preferably are paramagnetic or diamagnetic.

The electromagnets and the mechanical control of the present invention should be configured in such a way that the force field (electromagnetic, magnetic or ferromagnetic) is active only in that region of the syringe which is filled with the contrast agent. For example, if the plunger moves in the distal (i.e., forward) direction, only those regions of the electromagnets which lie in the distal direction of the syringe with respect to the plunger may be activated. The intensity and frequency of the movement has to be controlled, in accordance with the sensitivity of the contrast agent and in accordance with the movement sequence, in such a way that the consistency of the particles in the ultrasound contrast agent is not adversely affected.

The agitation element should preferably be controlled in such a way that sufficient homogenization is ensured but the particles in the ultrasound contrast agent are not destroyed by transverse forces. Sensors that monitor the movement of the force field and preferably also of the plunger may be used in order to ensure optimum mixing.

Turning now to the drawings of the preferred embodiments, FIG. 1 illustrates a syringe 1 having a plunger 2 disposed therein and a needle attachment end 3. The syringe 1 is connected to an injector 5 via a holder 4. The syringe 1 can be inserted into the holder 4 in a reversible manner.

The injector 5 comprises a ram 6 which is connected to the plunger 2 of the syringe 1. The ram 6 is moved with respect to the housing of the injector 5 by a motor 7, the motor turning a ring 8 which has a screw thread and surrounds the ram 6, which likewise has a complementary screw thread. The ring 8 is rotatable with respect to the housing.

A magnet 9, preferably a permanent magnet, can be moved with respect to the syringe 1 and a collar 11 by means of a linkage 10, the collar forming part of the injector 5. The collar 11 may also be attached to an injector 5 as an accessory. The linkage 10, which preferably comprises a toothed rack, is moved by a thrust motor 12, a pinion of which engages the toothed rack. The movement of the thrust motor 12 is controlled by a control device 13. In so doing, it is possible to take into account individually the nature of the contrast agent, the syringe size, the volume per minute of the injection and the stress on the patient.

At the distal end 3 of the syringe 1, the syringe 1 comprises a bulged recess 14 which is able to accommodate an agitation element 15. Preferably, the agitation element 15 is in the form of a ball. During an injection procedures, but before the syringe 1 is completely emptied of the fluid contained therein, the control system 13 operates to adjust the position of the ball 15 in such a way that the ball 15 can slide into the recess 14 to allow the plunger 2 to travel completely toward the needle attachment end or distal end 3 of the syringe to discharge the contents therefrom.

FIG. 2 illustrates a syringe 1 having a plunger 2 disposed therein and a needle attachment end 3. The syringe 1 is connected to an injector 5 via a holder 4. The syringe 1 can be inserted into the holder 4 in a reversible manner. The injector 5 has a ram 6 which is connected to the plunger 2 of the syringe 1. The ram 6 is moved with respect to the housing of the injector 5 by a motor 7, the motor turning a ring 8 which has a screw thread and surrounds the ram 6, which likewise has a complementary screw thread. The ring 8 is rotatable with respect to the housing.

A multiplicity of coils 16, through which current preferably can flow separately from one another, surround the syringe in a magnetic collar 17, the magnetic collar forming part of the injector 5. The magnetic collar 17 may also be attached to an injector 5 as an accessory. The coils 16 are individually activated by a control unit 18, so that a magnetic field can continuously change its position with respect to the syringe 1.

The magnetic field moves an agitation element 15, which is preferably in the form of a ball, within the syringe 1. The plunger 2 comprises, at the end facing toward the needle attachment end 3, a recess 20 that is able to accommodate the ball 15. The control unit 18 is controlled by means of the control device 13. In so doing, it is possible to take into account individually the nature of the contrast agent, the size of the syringe, the volume per minute of the injection and the stress to the patient.

EXAMLES

For Levovist® 200 mg/ml ultrasound contrast fluid, which is manufactured by Schering AG of Berlin, Germany, phase separation occurs within a couple of minutes (approximately 3–5 minutes) after preparation. This phase separation is characterized by contrast particles aggregating at the lower part of a syringe containing the contrast fluid and the watery diluent collecting above the contrast particles within the syringe.

A number of technical approaches to mitigating and/or preventing Levovist™ phase separation were tested using a standardized laboratory model. In the first technical approach, a small ferromagnetic ball (having a higher specific weight then Levovist™) was placed in a syringe and moved therein by means of a magnetic field applied thereto. In the second technical approach, an agitation element (having a higher specific weight then Levovist™) was placed in the syringe and moved therein by means of an external magnetic bar moved outside of and relative to the syringe.

Test Setup

The tests were conducted using in-vitro test equipment validated to simulate in-vivo contrast enhancement conditions. The test equipment allowed reproducible measurements of the enhancement characteristics of ultrasound contrast fluid suspensions.

Through the controlled movement or control of a magnetic field source, agitation elements placed in the syringe were able to be moved in a controlled fashion to agitate the ultrasound contrast fluid to prevent phase separation. After agitation, the ultrasound contrast fluid was injected into the testing equipment using a transfer tube and a 22 G needle. The simulated body temperature was 37° C. and the simulated negative pressure of the lung simulating component (i.e., oxygenator) of the testing equipment was 100 mBar.

Testing Method

Respective measurements of the enhancement properties of the ultrasound contrast fluid suspension over a prolonged period of time (up to 22 minutes) were conducted for syringes having magnetic agitation elements and for syringes not incorporating magnetic agitation elements. A standard infusion/injection speed of 1 ml/min was used throughout the tests. The impact of the phase separation mitigation approaches were deducted from the variances in the measured Doppler-signal intensity.

Results—Test One

Figure 3:
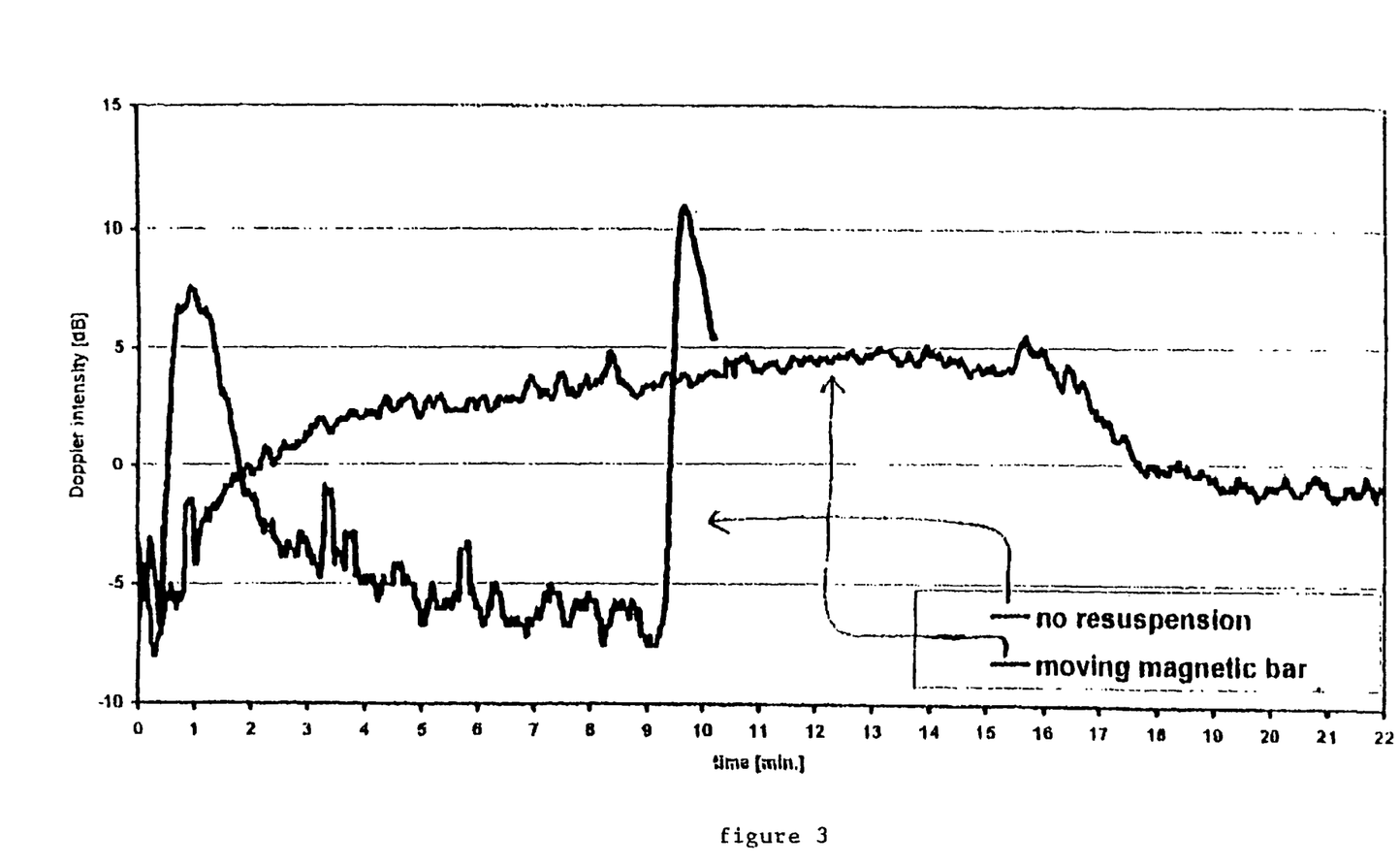
FIG. 3 is a graphical view comparing the Doppler signal intensity of a contrast agent with resuspension versus that of the contrast agent with no resuspension.

As shown in FIG. 3, no agitation of the ultrasound contrast fluid suspension leads to significant unfavorable inconsistencies in the enhancement properties of the contrast fluid, which is not suitable for clinical applications. However, when a magnetic bar was used to agitate the ultrasound contrast fluid suspension within the syringe, by means of a magnetic source located outside of the syringe, the contrast fluid was resuspended and a long-lasting, stable enhancement pattern was achieved.

Results—Test Two

Figure 4:
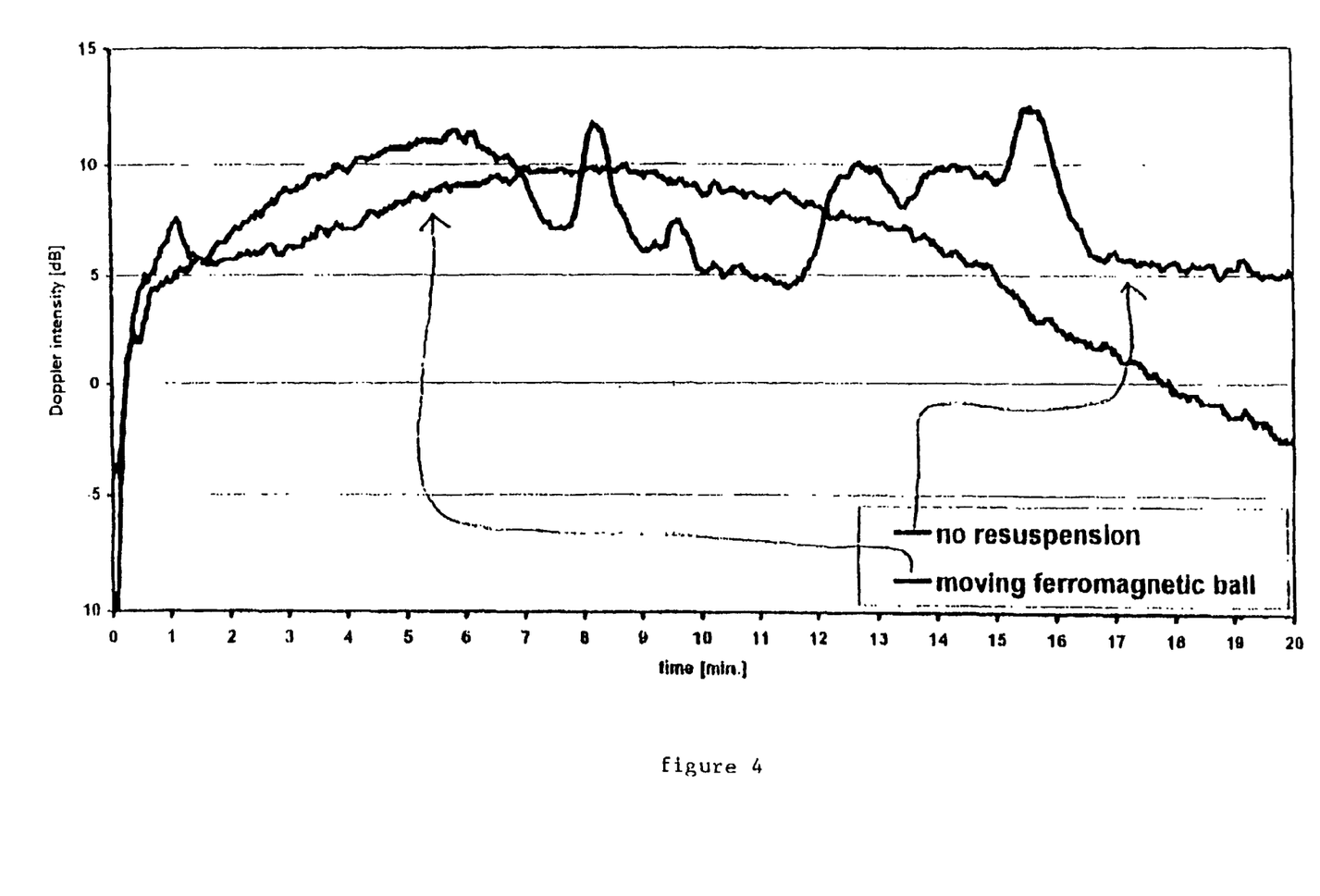
FIG. 4 is a graphical view comparing the Doppler signal intensity of a contrast agent with resuspension versus that of the contrast agent with no resuspension.

In this test, a ferromagnetic ball was moved within the syringe through application of an outside magnetic field. Again, as shown in FIG. 4, the test results clearly indicate that resuspension of the ultrasound contrast fluid suspension leads to significantly more consistent enhancement properties when compared to non-resuspended ultrasound contrast fluid suspension. With regard to the non-resuspended contrast fluid enhancement properties, the differences compared to Results—Test One (above) show that the extent and impact of phase separation on contrast enhancement is largely unpredictable.

Results—Test Three

Figure 5:
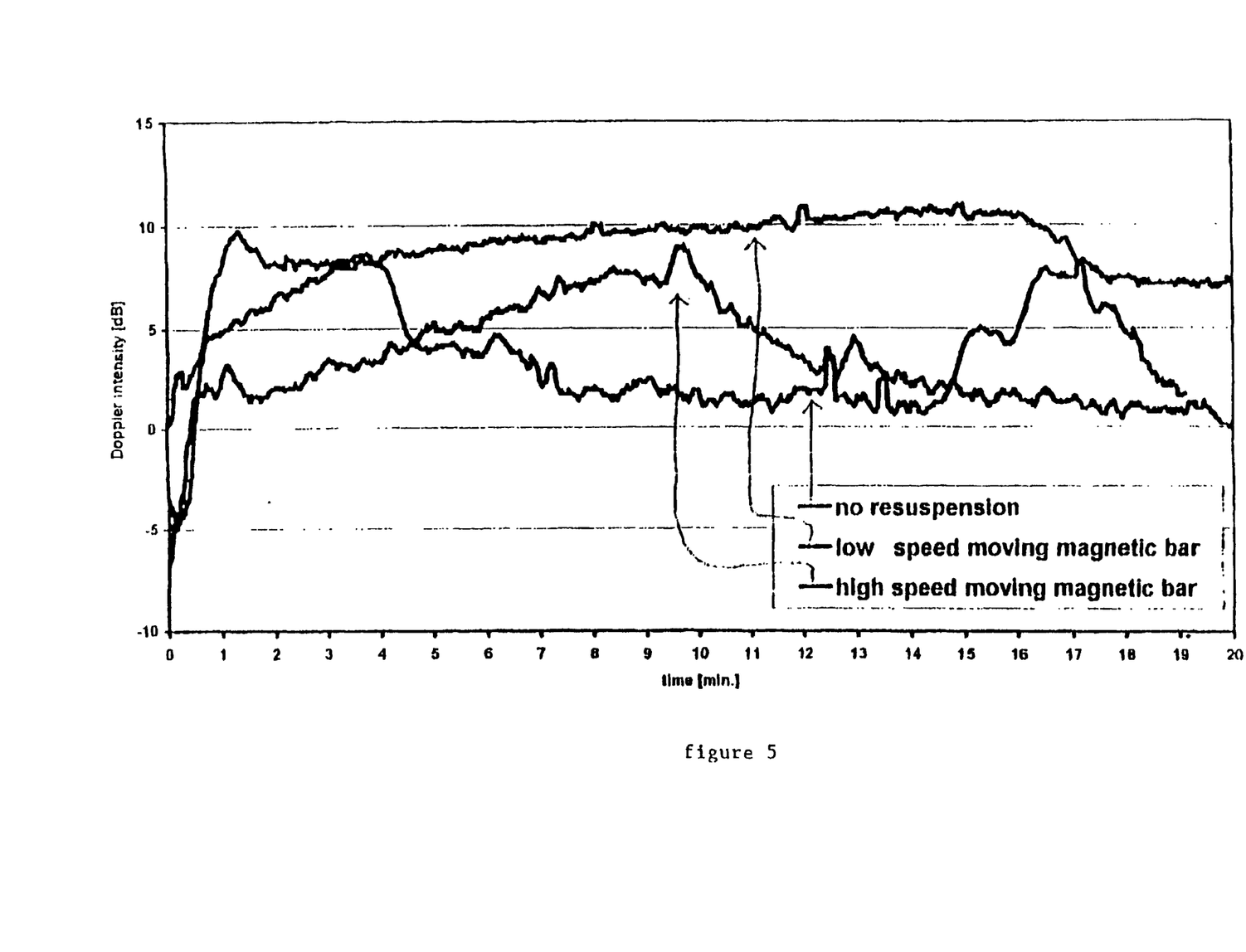
FIG. 5 is a graphical view comparing the Doppler signal intensity of a contrast agent with no resuspension versus that of the contrast agent with low-speed and high-speed resuspensions.

In this test, a magnetic bar was moved within the syringe through application of a ferromagnetic object outside the syringe. Besides a baseline comparison (i.e., compared to no resuspension of contrast fluid suspension), the influence of variations in the strength of the mechanical forces for resuspension were investigated. As can be clearly deducted from the test results as shown in FIG. 5, ultrasound contrast fluid suspensions contain fragile particles and the mechanical forces applied for resuspension must therefore be adjusted to the stability and strength of the contrast fluid suspension. An extremely vigorous resuspension is detrimental for the enhancement properties of the contrast fluid, whereas a slight agitation may not prevent phase separation. The key is to adjust the resuspension mode in way that the forces impacting the contrast fluid particles do not impair or limit their contrast enhancement purpose. The level of mechanical force required and/or tolerable for each individual ultrasound contrast fluid, including Levovist™ varies, but a reproducible and controllable resuspension mode is required.

It should be appreciated that the present invention may be configured as appropriate for the application. The embodiments and example described above are to be considered in all respects only as illustrative and not restrictive. The scope of the invention is indicated by the following claims, rather than by the foregoing description. All changes which fall within the meaning and range of equivalency of the claims are to be embraced within their scope.

List of reference numerals:
1. Syringe
2. Plunger
3. Needle attachment
4. Holder
5. Injector
6. Ram
7. Motor
8. Ring
9. Magnet
10. Linkage
11. Collar
12. Thrust motor
13. Control device
14. Bulge
15. Ball
16. Coils
17. Magnetic collar
18. Control unit
20. Plunger bulge

What is claimed is:

1. A syringe for use with an injector, comprising:
a body comprising a distal discharge end;
a plunger movably disposed within the body; and
at least one agitation element disposed within the body between the plunger and the distal discharge end, the at least one agitation element operable to be acted on by a magnetic field to agitate the contents of the syringe, the magnetic field being generated by a source operably associated with at least one of the syringe and the injector; and
an annular recess defined in the plunger or in the body adjacent to the distal discharge end thereof, the recess being adapted to accommodate the at least one agitation element.

2. The syringe of claim 1 wherein the contents of the syringe comprise a contrast agent.

3. The syringe of claim 2 wherein the contrast agent comprises an ultrasound contrast agent.

4. The syringe of claim 1 wherein the at least one agitation element comprises a ferromagnetic or magnetic element.

5. The syringe of claim 1 wherein the source comprises an electromagnetic field source.

6. The syringe of claim 5 wherein the source comprises one or more coils operably associated with the syringe.

7. The syringe of claim 1 wherein the source is operably associated with the injector and is moved mechanically outside the syringe.

8. The syringe of claim 7 wherein the source comprises a magnet or a ferromagnetic element.

9. The syringe of claim 1 wherein the at least one agitation element comprises a casing.

10. An injector system comprising:
an injector comprising means for mounting a syringe thereon;
a syringe comprising a body having a distal discharge end and means cooperable with the injector means for mounting the syringe on the injector, a plunger movably disposed within the body, at least one agitation element disposed within the body between the plunger and the distal discharge end, and an annular recess defined in the plunger or in the body adjacent to the distal discharge end thereof, the recess being adapted to accommodate the at least one agitation element; and
a field source operably associated with at least one of the syringe and injector, the field source operable to generate a magnetic field that acts on the at least one agitation element to agitate the contents of the syringe.

11. The injector system of claim 10 wherein the contents of the syringe comprise a contrast agent.

12. The injector system of claim 11 wherein the contrast agent comprises an ultrasound contrast agent.

13. The injector system of claim 10 wherein the at least one agitation element comprises a ferromagnetic or magnetic element.

14. The injector system of claim 10 wherein the field source comprises an electromagnetic field source.

15. The injector system of claim 14 wherein the field source comprises one or more coils operably associated with the syringe.

16. The injector system of claim 10 wherein the field source is operably associated with the injector and is moved mechanically outside the syringe.

17. The injector system of claim 16 wherein the field source comprises a magnet or a ferromagnetic element.

18. A method for agitating the contents of a syringe, comprising:
providing an injector comprising means for mounting a syringe thereon;
providing a syringe comprising a body having a distal discharge end and means cooperable with the injector means for mounting the syringe on the injector, a plunger movably disposed within the body, and at least one agitation element disposed within the body between the plunger and the distal discharge end;
providing a field source operably associated with at least one of the syringe and injector, the field source operable to generate a magnetic field that acts on the at least one agitation element to agitate the contents of the syringe;
activating the field source to generate the magnetic field;
applying the magnetic field to the at least one agitation element in the syringe; and
agitating the contents of the syringe with the at least one agitation element.

19. The method of claim 18, further comprising:
deactivating the field source to terminate the agitation of the syringe contents.

20. A syringe for use with an injector, the syringe comprising:
a body comprising a distal discharge end;
a plunger movably disposed within the body; and
at least one agitation element disposed within the body between the plunger and the distal discharge end, the at least one agitation element operable to be acted on by a magnetic field to agitate the contents of the syringe, the magnetic field being generated by an electromagnetic field source comprising one or more coils operably associated with the syringe.

21. The syringe of claim 20 wherein the contents of the syringe comprise a contrast agent.

22. The syringe of claim 21 wherein the contrast agent comprises an ultrasound contrast agent.

23. The syringe of claim 20 wherein the at least one agitation element comprises a ferromagnetic or magnetic element.

24. The syringe of claim 20 wherein the at least one agitation element comprises a casing.

25. The syringe of claim 20, further comprising a recess defined in at least one of the body of the syringe and the plunger of the syringe, the recess operable to accommodate the at least one agitation element.

26. The syringe of claim 25 wherein the recess is defined in the body of the syringe adjacent to the distal discharge end thereof.

27. The syringe of claim 25 wherein the recess is defined in the plunger of the syringe.

28. The syringe of claim 25 wherein the recess comprises an annular recess.

29. A syringe for use with an injector, the syringe comprising:
   a body comprising a distal discharge end;
   a plunger movably disposed within the body;
   at least one agitation element disposed within the body between the plunger and the distal discharge end, the at least one agitation element operable to be acted on by a magnetic field to agitate the contents of the syringe, the magnetic field being generated by a source operably associated with at least one of the syringe and the injector; and
   a recess defined in the body of the syringe adjacent to the distal discharge end thereof, the recess operable to accommodate the at least one agitation element.

30. The syringe of claim 29 wherein the contents of the syringe comprise a contrast agent.

31. The syringe of claim 30 wherein the contrast agent comprises an ultrasound contrast agent.

32. The syringe of claim 29 wherein the at least one agitation element comprises a ferromagnetic or magnetic element.

33. The syringe of claim 29 wherein the source comprises an electromagnetic field source.

34. The syringe of claim 33 wherein the source comprises one or more coils operably associated with the syringe.

35. The syringe of claim 29 wherein the source is operably associated with the injector and is moved mechanically outside the syringe.

36. The syringe of claim 35 wherein the source comprises a magnet or a ferromagnetic element.

37. The syringe of claim 29 wherein the at least one agitation element comprises a casing.

38. The syringe of claim 29 wherein the recess comprises an annular recess.

39. An injector system comprising:
   an injector comprising a syringe mounting device;
   a syringe comprising a body having a distal discharge end and an injector attachment device cooperable with the syringe mounting device for mounting the syringe on the injector, a plunger movably disposed within the body, and at least one agitation element disposed within the body between the plunger and the distal discharge end; and
   a field source operably associated with at least one of the syringe and injector, the field source operable to generate a magnetic field that acts on the at least one agitation element to agitate the contents of the syringe.

40. The injector system of claim 39 wherein the contents of the syringe comprise a contrast agent.

41. The injector system of claim 40 wherein the contrast agent comprises an ultrasound contrast agent.

42. The injector system of claim 39 wherein the at least one agitation element comprises a ferromagnetic or magnetic element.

43. The injector system of claim 39 wherein the field source comprises an electromagnetic field source.

44. The injector system of claim 43 wherein the field source comprises one or more coils operably associated with the syringe.

45. The injector system of claim 39 wherein the field source is operably associated with the injector and is moved mechanically outside the syringe.

46. The injector system of claim 45 wherein the field source comprises a magnet or a ferromagnetic element.

47. The injector system of claim 39, further comprising a recess defined in at least one of the body of the syringe and the plunger of the syringe, the recess operable to accommodate the at least one agitation element.

48. The injector system of claim 47 wherein the recess is defined in the body of the syringe adjacent to the distal discharge end thereof.

49. The injector system of claim 47 wherein the recess is defined in the plunger of the syringe.

50. The injector system of claim 47 wherein the recess comprises an annular recess.

51. An injector system comprising:
   an injector comprising a syringe mounting device;
   a syringe comprising a body having a distal discharge end and an injector attachment device cooperable with the syringe mounting device for mounting the syringe on the injector, a plunger movably disposed within the body, and at least one agitation element disposed within the body between the plunger and the distal discharge end; and
   an electromagnetic field source comprising one or more coils operably associated with the syringe, the field source operable to generate a magnetic field that acts on the at least one agitation element to agitate the contents of the syringe.

52. The injector system of claim 51 wherein the contents of the syringe comprise a contrast agent.

53. The injector system of claim 52 wherein the contrast agent comprises an ultrasound contrast agent.

54. The injector system of claim 51 wherein the at least one agitation element comprises a ferromagnetic or magnetic element.

55. The injector system of claim 51, further comprising a recess defined in at least one of the body of the syringe and the plunger of the syringe, the recess operable to accommodate the at least one agitation element.

56. The injector system of claim 55 wherein the recess is defined in the body of the syringe adjacent to the distal discharge end thereof.

57. The injector system of claim 55 wherein the recess is defined in the plunger of the syringe.

58. The injector system of claim 55 wherein the recess comprises an annular recess.

59. An injector system comprising:
   an injector comprising a syringe mounting device;
   a syringe comprising:
      a body comprising a distal discharge end, an injector attachment device cooperable with the syringe mounting device for mounting the syringe on the injector, and a recess defined therein adjacent to the distal discharge end;

a plunger movably disposed within the body; and at least one agitation element disposed within the body between the plunger and the distal discharge end, the recess operable to accommodate the at least one agitation element; and a field source operably associated with at least one of the syringe and injector, the field source operable to generate a magnetic field that acts on the at least one agitation element to agitate the contents of the syringe.

60. The injector system of claim 59 wherein the contents of the syringe comprise a contrast agent.

61. The injector system of claim 60 wherein the contrast agent comprises an ultrasound contrast agent.

62. The injector system of claim 59 wherein the at least one agitation element comprises a ferromagnetic or magnetic element.

63. The injector system of claim 59 wherein the field source comprises an electromagnetic field source.

64. The injector system of claim 63 wherein the field source comprises one or more coils operably associated with the syringe.

65. The injector system of claim 59 wherein the field source is operably associated with the injector and is moved mechanically outside the syringe.

66. The injector system of claim 65 wherein the field source comprises a magnet or a ferromagnetic element.

67. The injector system of claim 59 wherein the recess comprises an annular recess.

68. A method for agitating the contents of a syringe comprising a body having a distal discharge end, a plunger movably disposed within the body, and at least one agitation element disposed within the body between the plunger and the distal discharge end, the method comprising:

providing a field source operable to generate a magnetic field that acts on the at least one agitation element in the syringe;

activating the field source to generate the magnetic field;

applying the magnetic field to the at least one agitation element in the syringe; and agitating the contents of the syringe with the at least one agitation clement.

69. The method of claim 68, further comprising:

deactivating the field source to terminate the agitation of the syringe contents.

70. The method of claim 68 wherein the field source comprises an electromagnetic field source comprising one or more coils operably associated with the syringe.

71. The method of claim 68 wherein the syringe further comprises a recess defined in at least one of the body of the syringe and the plunger of the syringe, the recess operable to accommodate the at least one agitation element.

72. The method of claim 71 wherein the recess is defined in the body of the syringe adjacent to the distal discharge end thereof.

73. The method of claim 71 wherein the recess comprises an annular recess.

74. The method of claim 68 wherein the contents of the syringe comprise a contrast agent.

\* \* \* \* \*